US009084684B2

(12) United States Patent
Castro

(10) Patent No.: US 9,084,684 B2
(45) Date of Patent: Jul. 21, 2015

(54) STABILIZER FOR ASSISTING STABILIZATION OF A SPINAL IMPLANT

(71) Applicant: IGIP, LLC, Louisville, KY (US)

(72) Inventor: Frank P. Castro, Louisville, KY (US)

(73) Assignee: IGIP, LLC, Louisville, KY (US)

( * ) Notice: Subject to any disclaimer, the term of this patent is extended or adjusted under 35 U.S.C. 154(b) by 213 days.

(21) Appl. No.: 13/898,554

(22) Filed: May 21, 2013

(65) Prior Publication Data

US 2013/0268079 A1    Oct. 10, 2013

Related U.S. Application Data

(63) Continuation-in-part of application No. 12/927,050, filed on Nov. 6, 2010, now abandoned.

(51) Int. Cl.
*A61F 2/44* (2006.01)
*A61B 17/70* (2006.01)
*A61F 2/30* (2006.01)

(52) U.S. Cl.
CPC .............. *A61F 2/446* (2013.01); *A61B 17/7059* (2013.01); *A61F 2/44* (2013.01); *A61F 2/442* (2013.01); *A61F 2/4455* (2013.01); *A61F 2/4465* (2013.01); *A61F 2/30744* (2013.01); *A61F 2002/3013* (2013.01); *A61F 2002/30034* (2013.01); *A61F 2002/30062* (2013.01); *A61F 2002/30121* (2013.01); *A61F 2002/30146* (2013.01); *A61F 2002/30158* (2013.01); *A61F 2002/30159* (2013.01); *A61F 2002/30228* (2013.01); *A61F 2002/30235* (2013.01); *A61F 2002/30271* (2013.01); *A61F 2002/30311* (2013.01); *A61F 2002/30433* (2013.01); *A61F 2002/30517* (2013.01); *A61F 2002/30578* (2013.01); *A61F 2002/30607* (2013.01); *A61F 2002/30616* (2013.01); *A61F 2002/30785* (2013.01); *A61F 2002/4475* (2013.01); *A61F 2310/00017* (2013.01); *A61F 2310/00023* (2013.01)

(58) Field of Classification Search
CPC ........ A61F 2/4455; A61F 2/446; A61F 2/447
USPC ............................................ 623/17.11–17.16
See application file for complete search history.

(56) References Cited

U.S. PATENT DOCUMENTS

| 4,553,273 | A  | * | 11/1985 | Wu ............................... 623/23.45 |
| 4,657,550 | A  | * | 4/1987  | Daher ........................ 623/17.11 |
| 4,961,740 | A  |   | 10/1990 | Ray et al. |
| 5,290,312 | A  | * | 3/1994  | Kojimoto et al. .......... 623/17.15 |
| 5,571,192 | A  | * | 11/1996 | Schonhoffer .............. 623/17.11 |
| 5,702,453 | A  | * | 12/1997 | Rabbe et al. ............... 623/17.16 |
| 5,702,455 | A  | * | 12/1997 | Saggar ........................ 623/17.15 |
| 5,989,290 | A  | * | 11/1999 | Biedermann et al. ...... 623/17.11 |
| 6,190,413 | B1 | * | 2/2001  | Sutcliffe .................... 623/17.11 |
| 6,193,756 | B1 | * | 2/2001  | Studer et al. ............... 623/17.15 |
| 6,200,348 | B1 | * | 3/2001  | Biedermann et al. ...... 623/17.11 |
| 6,344,057 | B1 | * | 2/2002  | Rabbe et al. ............... 623/17.11 |
| 6,582,432 | B1 |   | 6/2003  | Michelson |
| 6,730,088 | B2 | * | 5/2004  | Yeh .............................. 606/247 |

(Continued)

*Primary Examiner* — Eduardo C Robert
*Assistant Examiner* — Stuart S Bray
(74) *Attorney, Agent, or Firm* — Kenneth F. Pearce

(57) ABSTRACT

A stabilizer for receiving an end of a spinal implant. The stabilizer includes a gap that creates a socket for receiving the spinal implant. Bodies of the stabilizer are manufactured in a plurality of shapes. A cover is capable of blocking egress of the spinal implant from the socket.

20 Claims, 13 Drawing Sheets

(56) References Cited

U.S. PATENT DOCUMENTS

| | | |
|---|---|---|
| 6,783,547 B2 | 8/2004 | Castro |
| 6,991,653 B2 * | 1/2006 | White et al. ............... 623/17.16 |
| 7,056,343 B2 * | 6/2006 | Schafer et al. ............. 623/17.11 |
| 7,156,874 B2 * | 1/2007 | Paponneau et al. ........ 623/17.11 |
| 7,235,105 B2 | 6/2007 | Jackson |
| 7,544,208 B1 * | 6/2009 | Mueller et al. ............. 623/17.15 |
| 7,758,648 B2 * | 7/2010 | Castleman et al. ........ 623/17.16 |
| 7,879,096 B2 * | 2/2011 | Dickson et al. ............ 623/17.11 |
| 7,981,157 B2 * | 7/2011 | Castleman et al. ........ 623/17.15 |
| 8,016,887 B1 * | 9/2011 | Castro ........................ 623/17.11 |
| 8,142,435 B2 * | 3/2012 | Refai et al. ................. 606/86 A |
| 8,142,441 B2 * | 3/2012 | Refai et al. ...................... 606/99 |
| 8,182,537 B2 * | 5/2012 | Refai et al. ................. 623/17.16 |
| 8,187,331 B2 * | 5/2012 | Strohkirch et al. ........ 623/17.16 |
| 8,197,546 B2 * | 6/2012 | Doubler et al. ............ 623/17.15 |
| 8,475,533 B1 * | 7/2013 | Castro ........................ 623/17.16 |
| 8,986,383 B2 * | 3/2015 | Castro ........................ 623/17.11 |
| 2003/0083746 A1 | 5/2003 | Kuslich |
| 2003/0120274 A1 * | 6/2003 | Morris et al. .................... 606/61 |
| 2003/0191531 A1 * | 10/2003 | Berry et al. ................ 623/17.11 |
| 2003/0195632 A1 | 10/2003 | Foley et al. |
| 2004/0088054 A1 | 5/2004 | Berry |
| 2004/0122518 A1 | 6/2004 | Rhoda |
| 2004/0153160 A1 * | 8/2004 | Carrasco .................... 623/17.15 |
| 2004/0225360 A1 * | 11/2004 | Malone ...................... 623/17.11 |
| 2004/0249377 A1 * | 12/2004 | Kaes et al. ...................... 606/61 |
| 2005/0090898 A1 * | 4/2005 | Berry et al. ................ 623/17.11 |
| 2005/0113921 A1 * | 5/2005 | An et al. .................... 623/17.11 |
| 2005/0256582 A1 | 11/2005 | Ferree |
| 2006/0058879 A1 * | 3/2006 | Metz-Stavenhagen .... 623/17.15 |
| 2006/0276899 A1 * | 12/2006 | Zipnick et al. ............ 623/17.13 |
| 2006/0276901 A1 * | 12/2006 | Zipnick et al. ............ 623/17.16 |
| 2007/0255409 A1 * | 11/2007 | Dickson et al. ............ 623/17.11 |
| 2008/0058939 A1 | 3/2008 | Hughes et al. |
| 2009/0036985 A1 * | 2/2009 | Whiting ..................... 623/17.11 |
| 2009/0138083 A1 * | 5/2009 | Biyani ....................... 623/17.11 |
| 2009/0187245 A1 * | 7/2009 | Steiner et al. ............. 623/16.11 |

\* cited by examiner

FIG 12

| Providing a socket for receiving a coupling end of the spinal implant, wherein the socket comprises: a polygonal, cylindrical or elliptic cylindrical body surrounding a cavity; a first end comprising a gap for receiving the coupling end; a second end opposite the first end; and an extension extending beyond the second end, wherein the extension comprises a plurality of apertures for receiving fasteners |
|---|
⬇
| Anchoring the socket to bone |
|---|
⬇
| Attaching a cover to the extension, wherein after attachment to the extension, the cover is capable of: blocking fastener egress from a majority of the plurality of apertures; and blocking egress of the spinal implant from the socket. |
|---|

FIG 13

| Providing a socket for receiving a coupling end of the spinal implant, wherein the socket comprises: a polygonal, cylindrical or elliptic cylindrical body surrounding a cavity; a first end comprising a gap for receiving the coupling end; a second end opposite the first end; and an extension extending beyond the second end, wherein the extension comprises a plurality of apertures for receiving fasteners |
|---|
⬇
| Anchoring the socket to bone |
|---|
⬇
| Attaching a cover to the extension, wherein after attachment to the extension, the cover is capable of: blocking fastener egress from a majority of the plurality of apertures; and blocking egress of the spinal implant from the socket. |
|---|
⬇
| Using fasteners to attach the cover to the extension |
|---|

FIG 14

Providing a socket for receiving a coupling end of the spinal implant, wherein the socket comprises: a polygonal, cylindrical or elliptic cylindrical body surrounding a cavity; a first end comprising a gap for receiving the coupling end; a closed second end opposite the first end; and an extension extending beyond the second end, wherein the extension comprises a plurality of apertures for receiving fasteners

⇩

Anchoring the socket to bone

⇩

Attaching a cover to the extension, wherein after attachment to the extension, the cover is capable of: blocking fastener egress from a majority of the plurality of apertures; and blocking egress of the spinal implant from the socket.

⇩

Using fasteners to attach the cover to the extension

STABILIZER FOR ASSISTING STABILIZATION OF A SPINAL IMPLANT

This Application is a Continuation-In-Part of pending U.S. application for Letters Patent entitled—Stabilizer for Assisting Stabilization of a Spinal Implant and Method of Using the Stabilizer—Ser. No. 12/927,050 filed on Nov. 6, 2010. By reference, Applicant incorporates application Ser. No. 12/927,050 into this Application.

BACKGROUND OF THE INVENTION

1. Field of the Invention

Among other things, the present invention is related to a stabilizer for a spinal implant. Preferred embodiments of the current invention have a gap for creating a socket for receiving a lengthwise end of the spinal implant. In the practice of the current invention, the stabilizer's body is fastened to vertebra. The stabilizer's cover is attachable to the body and blocks egress of the spinal implant from the socket as well egress of the fasteners securing the stabilizer's body to vertebra. Preferred embodiments of stabilizers are manufactured in many geometric shapes and can be utilized with a plethora of spinal implants.

2. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) U.S. Pat. No. 4,961,740-Ray, et al. enables a V-thread fusion cage and method of fusing a bone joint. In part, Column 6 of Ray reads, "The fusion basket 10 of FIG. 1 was formed from a solid steel cylinder by drilling eight small, equally spaced holes 11 in the axial direction, each hole being centered on a circle concentric with the axis of the cylinder. Then a large hole was drilled centered on the axis and having a radius substantially identical to that of the aforementioned circle. A V-thread 12 was then machined in the external surface of the cylinder, thus opening through that surface a perforation 13 extending through the rounded valley 14 of the V-thread at each crossing of the valley and one of the small holes 11. A screw thread 15 was then machined in the internal surface of the fusion basket to threadably receive an end cap 16 that has apertures 18 similar to those of a salt shaker. Snap-on end caps would also be useful."

Among other things, U.S. Pat. No. 4,961,740 does not appear to disclose a stabilizer distinct from the spinal implant for stabilizing a spinal implant.

2) U.S. Pat. No. 6,344,057-Rabbe, et al. enables an adjustable vertebral body replacement. In part, Column 6 of Rabbe reads, "In one important feature of the cylindrical body 21, the opposite ends of the cylindrical wall 25 are formed into external threads 32. In one specific embodiment, the threads 32 extend from each opposite end over most of the total length of the threaded cylindrical body 21 and are configured to engage the threaded endplates 22. Each endplate includes a flange 35, which preferably assumes a shape to cover a substantial load-bearing area of the endplates of the adjacent intact vertebral bodies. A cylinder 37 is integrally formed with flange 35 to extend toward the threaded cylindrical body 21 when the endplates 22 are placed within the excised vertebral space. The cylinder 37 of each endplate includes a number of threaded openings 39 adapted to receive a set screw 24 therein."

Among other things, U.S. Pat. No. 6,344,057 does not appear to disclose a body distinct from a spinal cage where the body has a generally linear tunnel; first and second opposed ends; a gap in one of the opposed ends proximate the spinal cage such that a combination of the gap and the tunnel creates a socket securing the closest longitudinal end of the spinal cage; and an extension comprising a plurality of apertures extending beyond the body's end distal from the spinal cage; or a cover comprising an aperture aligning with one of the extension's apertures and attachable to the extension, where the attached cover blocks egress from a majority of the extension's apertures and blocks lateral egress of the spinal cage from the gap of the socket.

3) U.S. Pat. No. 6,582,432-Michelson enables a cap for use with artificial spinal fusion implant. In part, Column 8 of Michelson reads, "The open end 54 of the cylindrical implant 50 has an internal thread 51 for receiving a complementary cap 52 which has an external thread 58 for engaging the internal threads 51 of the cylindrical member 50. As shown in FIG. 5, cap 52 has an exposed exterior surface opposite an unexposed interior surface with a mid-longitudinal axis passing through the exterior and interior surface of the cap. A cross section of cap 52 along a plane parallel to the mid-longitudinal axis is at least in part convex along the exterior surface of cap 52. A second cross-section of cap 52 along a second plane parallel to the mid-longitudinal axis of cap 52 is curved along at least a portion of the exterior surface of cap 52 so that the curvature of the first and second cross-sections form a portion of a sphere. As shown in FIG. 4a, cap 52 has rounded edges in a plane transverse the mid-longitudinal axis of cap 52. The cap 52 has a hexagonal opening 59 for use with an alien wrench for tightening the cap."

Among other things, U.S. Pat. No. 6,582,432 does not appear to disclose a stabilizer including a socket that is distinct from the spinal implant for stabilizing a spinal implant.

4) U.S. Pat. No. 6,783,547-Castro enables an apparatus for fusing adjacent bone structures. In part, Column 5 of Castro reads, "With reference to FIGS. 13-15, apparatus 10 may further include end caps 60 which are mounted to one or both of the exposed longitudinal ends (depending whether outer cage or inner cage is provided with an end face) of the inner and outer cages 12, 14. Each end cap 60 includes peripheral collar 62 and insertion portion 64 depending from the collar 62. Collar 62 defines an enlarged cross-section relative to the longitudinal ends of inner and outer cages 12, 14 to engage the respective ends of the cages 12, 14. Insertion portion 64 includes a plurality of arcuate internal springs 66 depending axially from the collar 62. Internal springs 66 are adapted to flex inwardly upon positioning of end cap 60 within the respective cage, but, return outwardly under the influence of their resilient characteristics, to engage the inner surfaces of the inner or outer cages 12, 14, thereby securing the end cap 60 to the respective cage 12, 14. Arcuate springs 66 may be connected to collar 62 by conventional means and are preferably fabricated from a resilient plastic or metallic material. End cap 60 further defines central opening 68. End cap 60 is shown circular in cross-section for use with a circular inner and outer cage 12, 14 although it is appreciated that end cap 60 may be elliptical if desired. A plurality of spaced individual cone-shaped spikes 70 extend from collar 62 for penetrating the vertebral end plates when the apparatus is positioned within the intervertebral space."

Among other things, U.S. Pat. No. 6,783,547 does not appear to disclose a stabilizer including a socket that is distinct from the spinal implant for stabilizing a spinal implant.

5) U.S. Pat. No. 7,235,105-Jackson enables a threaded center line cage with winged end gap [cap] (sic). In part, Column 6 of Jackson reads, "Referring to FIGS. 1 and 13-16, the end cap 3 includes a center section 30 and wing sections 32 extending laterally of the center section 30 and curving in a posterior direction therefrom. The front of the end cap 3 is preferably sized, shaped and designed to follow the contour of the front or anterior edge of the vertebrae 6 and 7. The end cap 3 includes structure for securing it to the spacer member 2. The illustrated end cap 3 includes a pair of opposed resilient pawls 34 extending from a posterior surface 36 (FIG. 13) of the end cap 3 at the center section 30. The pawls 34 are positioned to engage recesses 38 (FIGS. 1 and 14) formed into the lateral surfaces 12 of the spacer member 2 by deforming as the end cap is slid over the anterior end of the spacer member (see FIG. 14) and then resiliently returning to a gripping shape (as seen in FIG. 15) to hold the end cap 3 on the spacer number 2. Alternatively, other structure or means for securing the end cap 3 to the spacer member 2 may be employed in the assembly 1."

Among other things, U.S. Pat. No. 7,235,105 does not appear to disclose a stabilizer including a socket that is distinct from the spinal implant for stabilizing a spinal implant.

6) US Pub. Patent Application 20030083746-Kuslich discloses a vertebral spacer for spinal stabilization. Paragraphs 63 and 64 of Kuslich read, "[0063] End caps 70 and 72 are comprised of an end cap body 74 and include an engagement surface 76. The engagement surface 76 may be defined by an engagement lip 78 such as is shown in FIG. 15 or alternatively as a pair of engagement members 80 and 82 which define a groove 84 such as is shown in FIGS. 10, 12 and 16. Other configurations of engagement surfaces may be utilized. [0064] As may be seen in FIG. 14, end caps 70 and 72 may be configured to have a variety of shapes to allow the second engagement surface 86 of the end cap to engage the surface 56 and 58 of a spinal body 52 and 54, regardless of the relative angle between the device 10 and spinal body 52 or 54. In addition, the end caps 70 and 72 may be provided in various sizes to allow a body 12 of a standard size and shape to be used in a wide variety of sizes of intervertebral spaces 60. In the various embodiments shown herein the end caps 70 and 72 may have a diameter equal to or larger than the diameter 100 (illustrated in FIG. 1) of the body 12."

Among other things, US Published Patent Application 20030083746 does not appear to disclose a body distinct from a spinal cage where the body has a generally linear tunnel; first and second opposed ends; a gap in one of the opposed ends proximate the spinal cage such that a combination of the gap and the tunnel creates a socket securing the closest longitudinal end of the spinal cage; and an extension comprising a plurality of apertures extending beyond the body's end distal from the spinal cage; or a cover comprising an aperture aligning with one of the extension's apertures and attachable to the extension, where the attached cover blocks egress from a majority of the extension's apertures and blocks lateral egress of the spinal cage from the gap of the socket.

7) US Pub. Patent Application 20040088054-Berry discloses a laterally expandable cage. Paragraph 22 of Berry reads, "[0022] A laterally expandable spinal implant 100 according to one embodiment of the present invention will now be described with reference to FIGS. 1-6. As shown in FIGS. 1 and 2, the implant 100 includes a central member or cage 102, a pair of lateral members or wings 104 that are adapted to laterally extend from the cage 102, and an expansion mechanism 106 (or means) that is operable to extend the wings 104. In the illustrated embodiment, the expansion mechanism 106 includes a turnbuckle or threaded shaft 108 that connects the wings 104 together. In other embodiments, the expansion mechanism can include hydraulic pistons, mechanical linkages, and the like. The shaft 108 includes a gear 110 that is centrally located on the shaft 108 between opposing threaded portions 112 and 114. In one embodiment, threads 116 on the threaded portions 112 and 114 are oppositely threaded (i.e., one is a left handed thread and the other is a right handed thread.) In one form of the present invention, the threads 116 of the threaded portions 112 and 114 have an equal pitch such that the wings 104 are able to extend from the central member 102 at the same rate. This ensures that the implant 100 has a symmetrical configuration, which in turn aids in centering the implant 100 over the vertebrae. The threaded portions 112 and 114 threadedly engage threaded openings 118 that are defined in each of the wings 104. In another embodiment, only one end of the shaft 108 is threaded, while the other end of the shaft 108 is unthreaded. With this embodiment, the wings 104 are still extended by rotating the shaft 108."

Among other things, US Published Patent Application 20040088054 does not appear to disclose a stabilizer including a socket that is distinct from the spinal implant for stabilizing a spinal implant.

8) US Pub. Patent Application 20040122518-Rhoda discloses an intervertebral implant. Paragraph 105 of Rhoda reads, "[0105] As shown in FIGS. 17-20, upper endcap 402 also includes two elongated bores 410 which can be filled with bone growth inducing substances to allow bony ingrowth and to further assist in the fusion of the adjacent vertebrae. Upper endcap 402 further includes a central bore 411 for receiving a fastening member, such as a screw. In addition, upper endcap 402, on its upper surface 405, has sections or areas having teeth 412 or similar gripping means to facilitate engagement of implant 400 with the end plates of the adjacent vertebra, and has sections or areas 414, 416 which are substantially smooth and devoid of any protrusions. Although in FIG. 17 sections 414, 416 are shown as extending along the entire length of upper endcap 402, from perimeter edge to perimeter edge, sections 414, 416 may extend only partially along the length of upper endcap 402. Sections 414, 416 are provided to assist the surgeon in anterior or lateral implantation of the implant as was discussed above with respect to sections 22, 24. As can be seen in FIGS. 18 and 21, upper endcap 402 has a generally rectangular protrusion 418 configured and dimensioned to interface and mate with a recess portion of the implant body or with the lower endcap. While protrusion 418 has been shown and described as generally rectangular, it can be appreciated that protrusion 418 can be any shape desired. A lower surface 407 surrounds the protrusion 418. Lower surface 407 is illustrated as surrounding and encircling completely protrusion 418, but it can be appreciated that lower surface 407 may only partially surround protrusion 418."

Among other things, US Published Patent Application 20040122518 does not appear to disclose a stabilizer including a socket that is distinct from the spinal implant for stabilizing a spinal implant.

9) US Pub. Patent Application 20040225360-Malone discloses devices and methods for facilitating controlled bone growth or repair. Paragraph 72, in part, of Malone reads, "Ends 24, 26 of the cage body 22 are provided with a non-perforated closure. In the illustrated embodiment, the anterior end 26 is closed by an integral non-perforated end wall 46, while there is provided a removable end cap 48 securable, by threaded attachment, friction fit or otherwise, to the posterior end 24 of the cage body 22. The end cap 48 may be provided with a recess 50 for receiving an insertion tool, for example if the end cap is made to threadably connect to the cage body, and there is preferably provided on the top of the end cap 48 a line score 52 for aiding proper orientation of the device in the vertebral interspace."

Among other things, US Published Patent Application 20040225360 does not appear to disclose a body distinct from a spinal cage where the body has a generally linear tunnel; first and second opposed ends; a gap in one of the opposed ends proximate the spinal cage such that a combination of the gap and the tunnel creates a socket securing the closest longitudinal end of the spinal cage; and an extension comprising a plurality of apertures extending beyond the body's end distal from the spinal cage; or a cover comprising an aperture aligning with one of the extension's apertures and attachable to the extension, where the attached cover blocks egress from a majority of the extension's apertures and blocks lateral egress of the spinal cage from the gap of the socket.

10) US Pub. Patent Application 20080058939-Hughes, et al. discloses a revision spacer. Paragraph 20 of Hughes reads, "The upper endplate module 32 includes an outer surface 38 and an inner surface 40 with passages 42 extending through the module 32 including through the outer and inner surfaces 38, 40. A keel 44 extends from the outer surface 38 and is adapted to engage the vertebral body 12 when the device 30 is inserted into the disc space 20. The upper endplate module 32 may further include access ports 45 to permit manipulation of the endplate module with an insertion or extraction tool. The ports 45 may also allow for eventual bone ingrowth. The upper endplate module 32 may also include one or more radiolucent markers 47 for monitoring the position of the device 30 during and after implantation using fluoroscopy.

Among other things, US Published Patent Application 20080058939 does not appear to disclose a stabilizer including a socket that is distinct from the spinal implant for stabilizing a spinal implant.

11) US Pub. Patent Application 20090138083-Biyani discloses a variable height vertebral body replacement implant. Paragraph 29 of Biyani reads, "Depending upon the anatomy of the patient, it maybe desirable to also provide a wedge-shaped end cap 124 on one or both of the end rings 115, 119. The respective end caps 124 each has a distal end surface 125 disposed at an angle A (see FIG. 8) in the range of 2° to 10° with respect to a plane P perpendicular to the axis X centered between the joined insertion rod sections 117 and hollow members 120. The end caps 124 can be fastened to the respective end rings 115, 119 by any desired fastening means. Each of the end caps 124 has a plurality of serrations or projections 128 extending from its distal end surface 125."

Among other things, US Published Patent Application 20090138083 does not appear to disclose does not appear to disclose a body distinct from a spinal cage where the body has a generally linear tunnel; first and second opposed ends; a gap in one of the opposed ends proximate the spinal cage such that a combination of the gap and the tunnel creates a socket securing the closest longitudinal end of the spinal cage; and an extension comprising a plurality of apertures extending beyond the body's end distal from the spinal cage; or a cover comprising an aperture aligning with one of the extension's apertures and attachable to the extension, where the attached cover blocks egress from a majority of the extension's apertures and blocks lateral egress of the spinal cage from the gap of the socket.

12) US Pub. Patent Application 20090187245-Steiner, et al. discloses an interbody fusion hybrid graft. Paragraph 35 of Steiner reads, "The composite cortical bone block body or intervertebral spacer 10 is preferably constructed with a first end cap member 12 constructed of cortical bone taken from donors cut into a ring shape. The cap member body 13 has an interior circular through going bore 14 formed or cut therein, and defines a flat planar bottom surface 16 which is provided with a dovetail shaped projection 18 which extends outward from the planar bottom surface 16. The cap body is tapered with the rear end 17 being of a greater height than the front end 19. The outer or top surface 20 which is tapered has a plurality of teeth 22 formed or cut into the exterior surface to provide a gripping surface on the adjacent vertebrae. The taper runs between 5° to 10° and the height of the upper cap member runs between 3-4 mm. The side wall of the ring body is formed with a channel or groove 24. The cortical cap members 12 and 112 have superior wall strength for support between load bearing body structures such as vertebrae. While it is noted that the bottom wall surfaces and are planar, these surfaces can be provided with any kind of complementary construction."

Among other things, US Published Patent Application 20090187245 does not appear to disclose a stabilizer including a socket that is distinct from the spinal implant for stabilizing a spinal implant.

13) U.S. Pat. No. 8,182,537-Refai, et al. enables a vertebral body replacement device and method for use to maintain a space between two vertebral bodies within a spine. In part, Column 4 of Refai reads, "Generally stated, disclosed herein is a vertebral body replacement device or vertebral spacer that typically includes a body member, a central rod member, a support ring, two end members and at least one footplate member . . . . As depicted in FIG. 1, the general arrangement of a vertebral body replacement device 10, in accordance with an aspect of the present invention, includes a body member 30, at least two end members 20, a central rod member 40 and a support ring 50 . . . . With reference to FIG. 1, vertebral body replacement device 10 includes body member 30, at least two end members 20 positioned superior and inferior relative to body member 30, a central rod member 40 for placement within body member 30 and support ring 50 that is configured to contact and secure central rod member 40 within body member 30. Exhibited in FIG. 1, body member 30 also includes an inner wall 31 and an outer wall 32, at least one hole 38 extending from outer wall 32 through inner wall 31. Further, body member 30 has at least one anti-rotational rib 35 disposed on and extending for substantially the entire length of outer wall 32. At least one rib 35 is oriented in a superior to inferior direction relative to body member 30 and substantially parallel to a longitudinal axis 72 of body member 30. At least one hole 38 is used for the placement of bone graft or other biocompatible material that will facilitate bone fusion to occur in vivo following implantation of the device."

Among other things, U.S. Pat. No. 8,182,537 does not appear to disclose a stabilizer distinct from the spinal implant for stabilizing a spinal implant. Further, Refai does not appear to disclose a body distinct from a spinal cage where the body has a generally linear tunnel; first and second opposed ends; a gap in one of the opposed ends proximate the spinal cage such that a combination of the gap and the tunnel creates a socket securing the closest longitudinal end of the spinal cage; and an extension comprising a plurality of apertures extending beyond the body's end distal from the spinal cage; or a cover comprising an aperture aligning with one of the extension's apertures and attachable to the extension, where the attached cover blocks egress from a majority of the extension's apertures and blocks lateral egress of the spinal cage from the gap of the socket.

14) US Published Patent Application 20030195632-Foley, et al. discloses a spinal implant with attached ligament. Paragraph 21 of Foley reads, [0021] Referring to FIG. 1, there is shown an implant according to one embodiment of the present invention. Although the rigid implants according to the present invention may have many uses, such as interbody fusion devices or vertebral replacement bodies, the embodiment shown in FIG. 1 is particularly adapted for promoting interbody fusion in the spine. Specifically, FIG. 1 illustrates a spinal implant 10 having a rigid body portion 12 that extends between a leading end 30 and a trailing end 32, and has a height H adapted for insertion into the disc space between adjacent vertebrae. Body portion 12 can be made from any biocompatible material known to those skilled in the art. Some examples include titanium, composite materials, including carbon composites, surgical stainless steel, to name a few, so long as the material provides body portion 12 sufficient structural integrity to support the spinal column load at the disc space where it is inserted. In one specific application, body portion 12 is a fusion device that provides for fusion between the adjacent vertebrae."

Among other things, US Published Patent Application 20030195632 does not appear to disclose a stabilizer distinct from the spinal implant for stabilizing a spinal implant.

15) US Published Patent Application 20050256582-Ferree discloses spinal implants, including devices that reduce pressure on the annulus fibrosis. Paragraph 231 of Ferree reads, "FIG. 1A is a lateral view of a "curtain" annulus augmentation device similar to the annulus augmentation devices taught in my U.S. Pat. No. 6,371,990, the entire content of which is incorporated herein by reference. Areas 102, 104 of the drawing represent spikes composed of titanium or other suitably rigid biocompatible material(s). The spikes slide into slots that are machined into the vertebrae. The section 110 of the device represents a dam, preferably constructed of a flexible, braided or mesh material such as nylon or Dacron. FIG. 1B is an anterior view of the embodiment of the invention drawn in FIG. 1A."

Among other things, US Published Patent Application 20050256582 does not appear to disclose a stabilizer distinct from the spinal implant for stabilizing a spinal implant.

SUMMARY OF THE INVENTION

The present invention provides a stabilizer capable of assisting the stabilization of the spinal implant after the load-bearing spinal implant is inserted into a surgically created cavity. Preferred embodiments of the current stabilizer include a body that is secured to bone. Within the scope of the present invention, the body includes a gap that creates a socket for receiving a lengthwise edge of the load-bearing spinal implant. In accord with the present invention, sockets can be manufactured in different shapes to accommodate the different shapes of the spinal implants. And a cover is attachable to the body to block egress, among other things, of the load-bearing spinal implant from the socket.

An aspect of a preferred embodiment of the present invention is to provide a stabilizer for assisting stabilization of a spinal implant.

Still another aspect of a preferred embodiment of the present invention is to provide a stabilizer including a gap therein for creating a socket for receiving a longitudinal end of the load-bearing spinal implant.

It is another aspect of a preferred embodiment of the present invention to provide a stabilizer with a polygonal shaped body capable of stabilizing amorphous or geometrically defined load-bearing spinal implants.

Yet another aspect of preferred embodiments the present invention is to provide stabilizers with cylindrical or elliptic cylindrical bodies capable of stabilizing amorphous or geometrically defined load-bearing spinal implants.

Yet still another aspect of preferred embodiments of the present invention is to provide stabilizers with rectangular, trapezoidal and/or hexagonal bodies capable of stabilizing amorphous or geometrically defined load-bearing spinal implants.

It is still another aspect of a preferred embodiment of the present invention to provide a stabilizer with a body including an extension that has a plurality of apertures.

Still another aspect of a preferred embodiment of the present invention is to provide a cover including an aperture for aligning with one of the plurality of apertures located in the body's extension.

It is another aspect of the present invention to provide an embodiment that utilizes a fastener to secure the cover to the body.

A preferred embodiment of the present invention can be described as a stabilizer for assisting stabilization of a spinal cage implanted into a surgically created cavity, to wherein the stabilizer is distinct from the spinal cage; the stabilizer comprising: a) a cylindrical or an elliptic cylindrical wall encircling a lumen, wherein the wall comprises a first lengthwise end, a second lengthwise end and a lengthwise axis; the wall further comprising: i) a rim at the first lengthwise end, wherein the rim is distal from a closest longitudinal end of the spinal cage; ii) an opening opposite the rim receiving the spinal cage; iii) a gap at the second lengthwise end opposite the first lengthwise through which the closest longitudinal end of the spinal cage is passable, wherein a combination of the gap and the wall creates a socket securing the longitudinal end of the spinal cage; and iv) an extension comprising a plurality of apertures and integral with the wall, wherein the extension is opposed to and coplanar with the gap and extends beyond the rim in a direction analogous to the lengthwise axis; b) a cover comprising an aperture aligning with one of the extension's apertures and attachable to the extension, wherein the attached cover: i) blocks egress from a majority of the extension's apertures; and ii) blocks lateral egress of the spinal cage from the gap of the socket; and c) fasteners securing the cover to the extension and the extension to vertebra.

Another preferred embodiment of the present invention can be described as a stabilizer assisting stabilization of a load-bearing spinal implant implanted into a surgically created cavity; the stabilizer comprising a body distinct from the load-bearing spinal implant; the body further comprising: a) a wall surrounding a lumen, wherein the wall further comprises: i) first and second opposed lengthwise ends comprising openings corresponding to the lumen; ii) at least one rim distal from a closest longitudinal end of the load-bearing spinal implant; iii) a gap at one of the lengthwise ends proximate the load-bearing spinal implant through which the closest longitudinal end of the load-bearing spinal implant is passable, wherein a combination of the gap and the wall creates a socket securing the closest longitudinal end of the load-bearing spinal implant; and iv) an extension comprising a plurality of apertures, wherein the extension is opposed to the gap and extends beyond at least one rim in a direction similar to the lengthwise axis; b) a cover comprising an aperture aligning with one of the extension's apertures and attachable to the extension, wherein the attached cover: i) blocks egress from a majority of the extension's apertures; and ii) blocks lateral egress of the load-bearing spinal implant from the gap of the socket; and c) fasteners securing the cover to the extension and the extension to vertebra.

Yet preferred another embodiment of the present invention can be described as a stabilizer assisting stabilization of a spinal cage implanted into a surgically created cavity; the stabilizer comprising: a) a body distinct from the spinal cage; the body comprising: i) a generally linear tunnel including a lengthwise axis, wherein the lengthwise axis runs in a similar direction with a longitudinal axis of the spinal cage; ii) first and second opposed ends; iii) a gap in one of the opposed ends proximate to the spinal cage through which the closest longitudinal end of the spinal cage is passable such that a combination of the gap and the tunnel creates a socket securing a closest longitudinal end of the spinal cage; and iv) an extension comprising a plurality of apertures and integral with the body, wherein the extension is opposed to and coplanar with the gap and extends beyond one of the opposed ends distal from the spinal cage in a direction analogous to the lengthwise axis; b) a cover comprising an aperture aligning with one of the extension's apertures and attachable to the extension, wherein the attached cover: i) blocks egress from a majority of the extension's apertures; and ii) blocks lateral egress of the spinal cage from the gap of the socket; and c) fasteners securing the cover to the extension and the extension to vertebra.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 12 is an exemplification of the steps of an embodiment of the current method of using the stabilizer for assisting the stabilization of a load-bearing spinal implant.

FIG. 13 is a diagrammatic representation of the steps of another embodiment of the current method of using the stabilizer for assisting the stabilization of a load-bearing spinal implant.

FIG. 14 is another diagrammatic representation of the steps of still another embodiment of the current method of using the stabilizer for assisting the stabilization of a load-bearing spinal implant.

DESCRIPTION OF THE PREFERRED EMBODIMENTS

Figure 1:
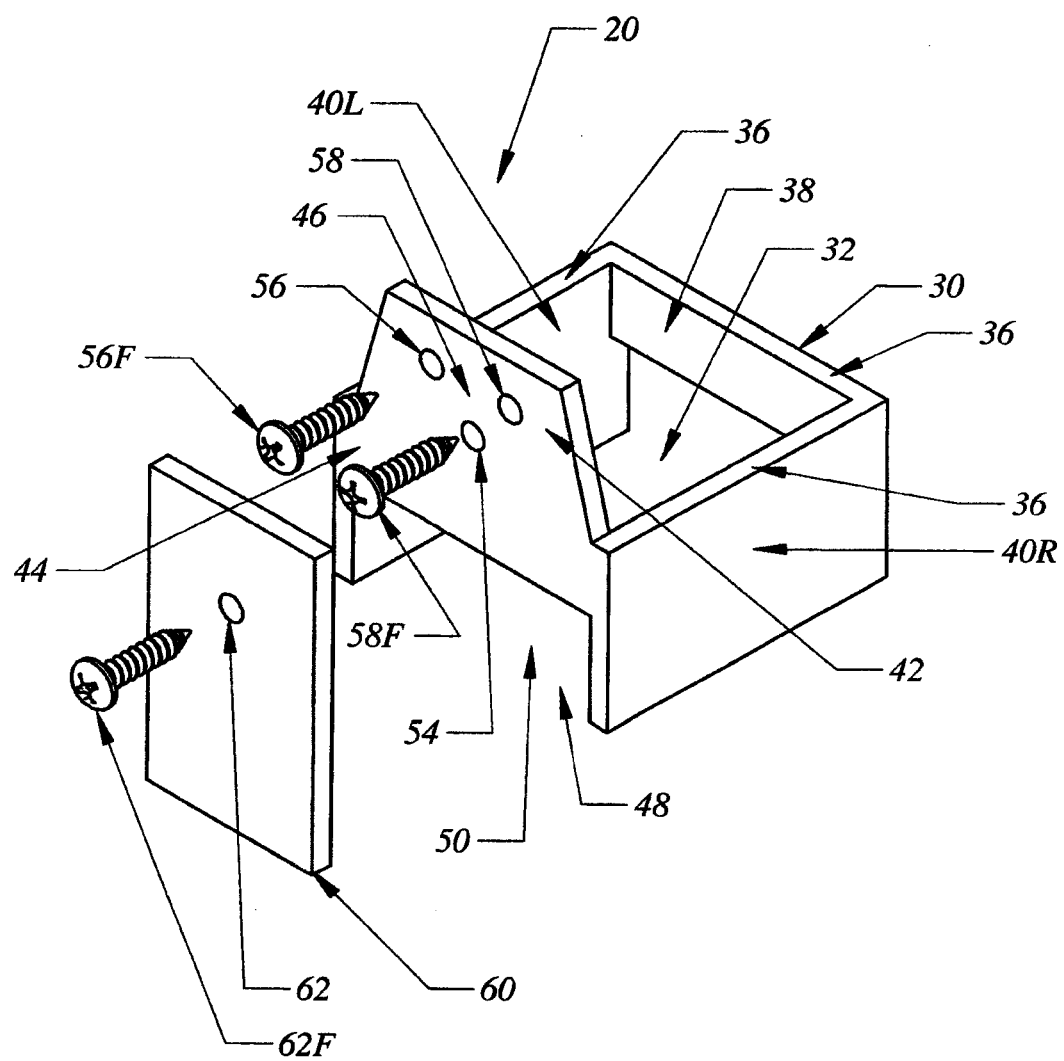
FIG. 1 is an exploded view frontal perspective of a preferred embodiment of the stabilizer (20) having a polygonal body (30) and attachable cover (60).

Although the disclosure hereof is detailed to enable those skilled in the art to practice the invention, the embodiments published herein merely exemplify the present invention.

The practice of the present invention requires the removal of mammalian tissue to create a cavity for receiving a load-bearing spinal implant. Depending on the surgical procedure performed, load-bearing spinal implants of varying sizes and shapes may be selected for eventual implantation into the surgical cavity. The current invention can be utilized with load-bearing spinal implants, such as cages, live or cadaver bone graphs or biomaterials where the load-bearing spinal implants are distinct from the stabilizer. Preferred embodiments of the current stabilizer are manufactured in differing sizes and shapes and are compatible with numerous load-bearing amorphous or geometrically defined spinal implants.

As used herein, after the load-bearing spinal implant is implanted into the surgically created cavity, a load-bearing spinal implant shall mean a spinal implant that is immediately capable of withstanding forces associated with supporting the spine in a manner similar to a normal spine prior to disease or injury. Further, a load-bearing spinal implant utilized with the current invention is of adequate span to run the approximate distance between opposed vertebral sections found at each longitudinal end of the surgically created cavity. Within the scope of the present invention, the current stabilizer is not a load bearing body capable of spanning the length of the surgically created cavity. Instead the current stabilizer can be utilized to stabilize the first end of the load-bearing spinal implant, the second end of the load-bearing spinal implant or both ends of the load-bearing spinal implant.

In the most general sense, the current invention is a stabilizer for assisting with the stabilization of a spinal implant that will be implanted into the surgically created cavity. Stabilizers in accord with the present invention can have polygonal, cylindrical, generally cylindrical, elliptic cylindrical or generally elliptic cylindrical bodies. When engineering parameters require, the polygonal, generally cylindrical or generally elliptic bodies can include one or more nebulous segments. Select preferred embodiments of the stabilizer can be engineered to have a socket for fitting about an end of virtually any load-bearing spinal implant of various structural dimensions. Unless otherwise indicated, for the remainder of this specification: the term "cylindrical" body can also refer to a generally cylindrical body and the term "elliptic cylindrical" body can also refer to a generally elliptic cylindrical body.

For preferred embodiments, an anterior wall or extension of the body includes a plurality of apertures and extends beyond an outward edge of the polygonal, cylindrical or elliptic cylindrical body. Each stabilizer further includes a cover that has an aperture that can be aligned with one of the plurality of apertures positioned on the body's anterior wall or extension. Fasteners secure the cover to the polygonal, cylindrical or elliptic cylindrical body as well as vertebra. After attachment to the polygonal, cylindrical or elliptic cylindrical body, the cover is capable of preventing lateral egress of fasteners securing the stabilizer to bone. Stabilizers of the current invention can be manufactured of biocompatible metals, plastics or combinations thereof, and preferred embodiments are manufactured of titanium, titanium alloys, stainless steel, non-resorbable and resorbable polymers.

The current stabilizer meets the long felt but unfilled need of providing a stabilizer for use with a load-bearing spinal implant where the stabilizer is attached to vertebra at first end of the stabilizer and has a socket at the second end for connecting to a longitudinal end of the spinal implant. Thus, the current stabilizer meets the long felt but unfulfilled need of reducing, if not eliminating, possible lateral misalignment of the load-bearing spinal implant after implantation of the load-bearing spinal implant into the surgically created cavity. Preferred embodiments of the current stabilizer additionally meet the long felt but unfulfilled needs of blocking egress of fasteners attaching the body to vertebra from the body after the body's attachment to vertebra while simultaneous blocking lateral egress of the load-bearing spinal implant from the surgically created cavity. Applicant believes that the use of the current stabilizer with a load-bearing spinal implant reduces the possibility of spinal column damage after implantation of the load-bearing spinal implant into the surgically created cavity that may be due to any shifting of the load-bearing spinal implant after its implantation into the spinal column.

Figure 15:
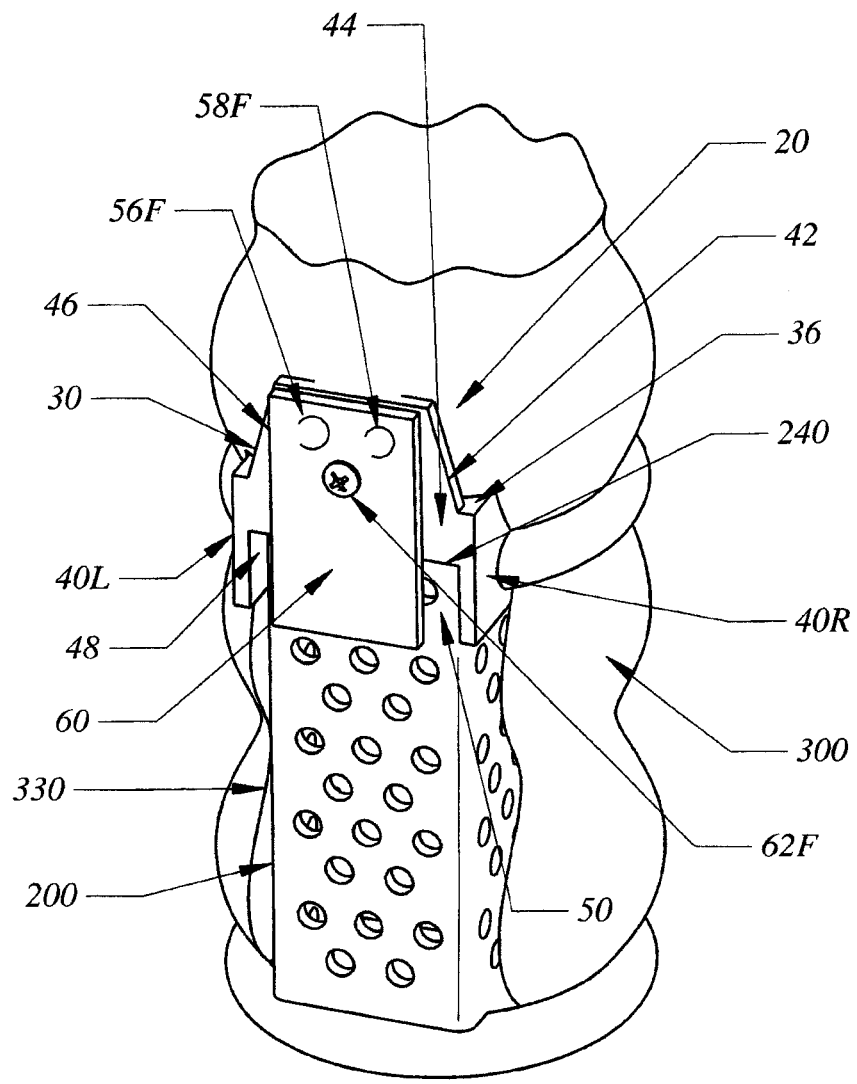
FIG. 15 is a frontal view of a preferred embodiment of a polygonal stabilizer (20) for assisting with stabilization of a load-bearing spinal implant (200).

FIG. 1 is an exploded view frontal perspective of a preferred embodiment of the stabilizer (20) having a polygonal body (30) and attachable cover (60). Polygonal body (30) encloses opening, cavity or tunnel (32). Perimeter (36) is distal from spinal implant (not shown in this view). Extending from perimeter (36) toward spinal implant are posterior wall (38) and lateral walls (40L and 40R). Posterior wall (38) and lateral walls (40L and 40R) extend approximately identical lengths from perimeter (36). As shown in FIGS. 1 and 15, anterior wall (42) has first section (44) extending from perimeter (36) toward the load-bearing spinal implant (200) and second section or extension (46) extending from perimeter (36) away from the load-bearing spinal implant (200) in a direction analogous to said lengthwise axis of body (30) and similar to a longitudinal axis of the load-bearing spinal implant (200). Since first section (44) is of lesser length than posterior wall (38) and lateral walls (40L and 40R), socket (50) for fitting about a lengthwise end of the spinal implant is created. A lengthwise end of the spinal implant can be fitted through gap (48) into socket (50). Second section (46) of anterior wall (42) is provided with apertures (54, 56 and 58). In select preferred embodiments, the combination of posterior wall (38), lateral walls (40L and 40R) and anterior wall (42) create an integral polygonal wall for body (30). As shown in FIG. 1, perimeter (36) is open to cavity (32), but in select preferred embodiments perimeter (36) can be a continuous surface such that one end of cavity or tunnel (32) is closed.

Cover (60) is provided with aperture (62) that upon attachment to polygonal body (30) aligns with aperture (54) of second section (46) of anterior wall (42). When cover (60) is attached to polygonal body (30), cover (60) prevents egress of fasteners (56F and 58F) from second section or extension (46) of polygonal body (30). Fastener (62F) secures cover (60) at aperture (54) to second section or extension (46) such that cover (60) blocks lateral egress of the spinal implant (not shown in this view) from gap (48) and socket (50).

Figure 2:
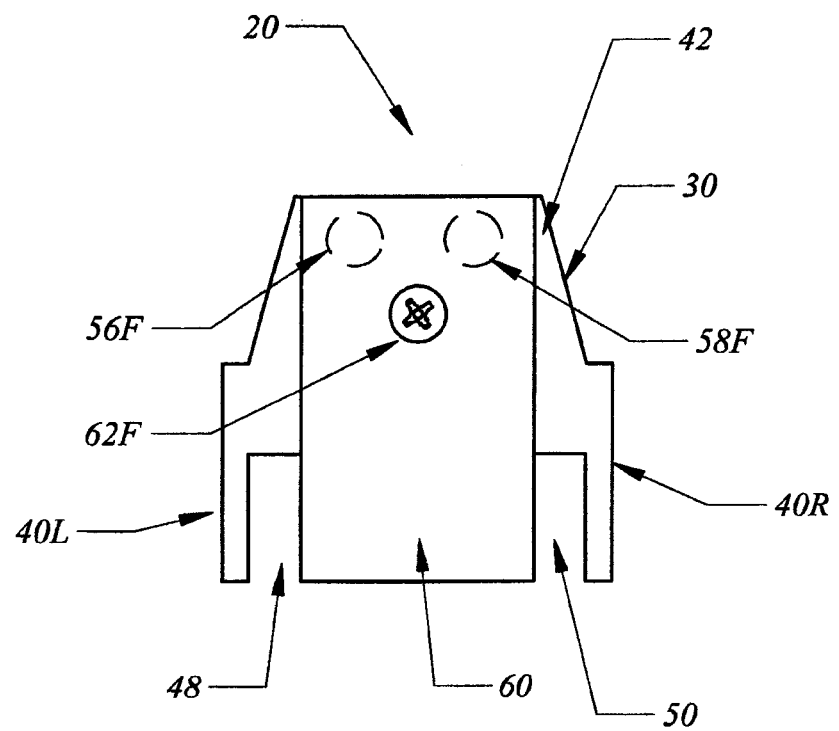
FIG. 2 is a frontal view a preferred embodiment of stabilizer (20) where cover (60) is attached to anterior wall (42) of polygonal body (30).

FIG. 2 is a frontal view of stabilizer (20) where cover (60) is attached to anterior wall (42) of polygonal body (30). Fastener (62) secures cover (60) to anterior wall to block egress of fasteners (56F and 58F) from apertures (56 and 58), respectively. Cover (60) is of sufficient length to block lateral egress of the spinal implant (not shown in this view) from gap (48) and socket (50).

Figure 3:
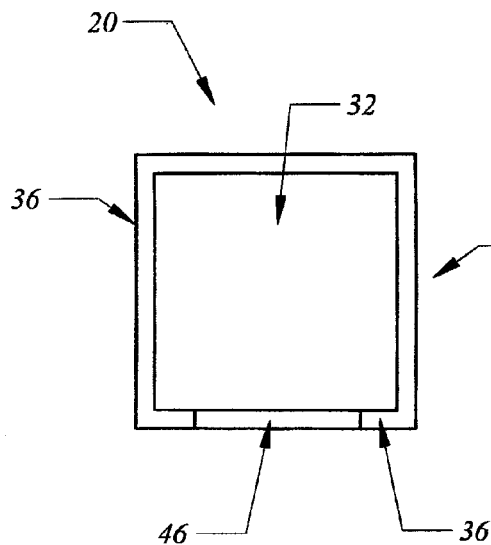
FIG. 3 portrays a rectangular polygonal body embodiment within the scope of the present invention.
Figure 4:
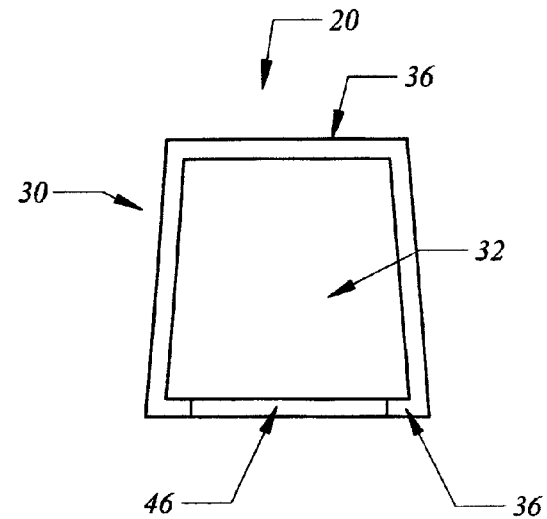
FIG. 4 shows a trapezoidal polygonal body embodiment within the scope of the current invention.
Figure 5:
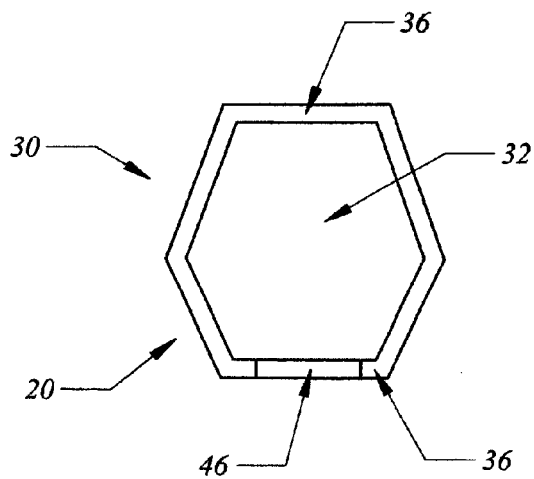
FIG. 5 enables a hexagonal polygonal body embodiment within the scope of the present invention.

By way of illustration and not limitation, FIGS. 3-5 are top plan views of preferred embodiments of stabilizers (20) with different shaped polygonal bodies (30). FIG. 3 portrays a polygonal body (30) with a rectangular wall. FIG. 4 shows a polygonal body (30) with a trapezoidal wall. FIG. 5 enables a polygonal body (30) with a hexagonal wall. Although not shown in FIGS. 3-5, depending on engineering parameters and the design of the spinal implant that will be fitted into the stabilizer's socket, polygonal bodies (30) of other shapes are within the scope of the present invention.

In the preferred embodiments displayed in FIG. 3-5, openings, cavities or tunnels (32), perimeters (36) and second sections or extensions (46) of anterior walls (42) are disclosed. For select preferred embodiments not shown in FIGS. 3-5, second sections (46) can be the depth of perimeter (36). In other words, second sections (46) of anterior walls (42) equate with the perimeters for depth and width of second sections (46).

Figures 3A, 4A:
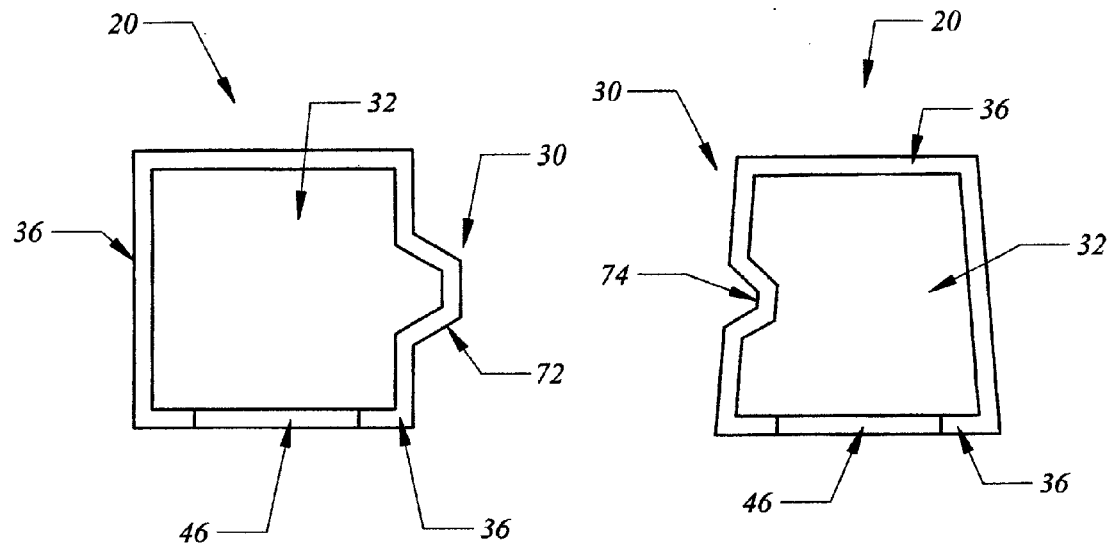
FIG. 3A portrays a nebulous rectangular polygonal body embodiment within the scope of the present invention.
FIG. 4A shows a nebulous trapezoidal polygonal body embodiment within the ambit of the current invention.
Figure 5A:
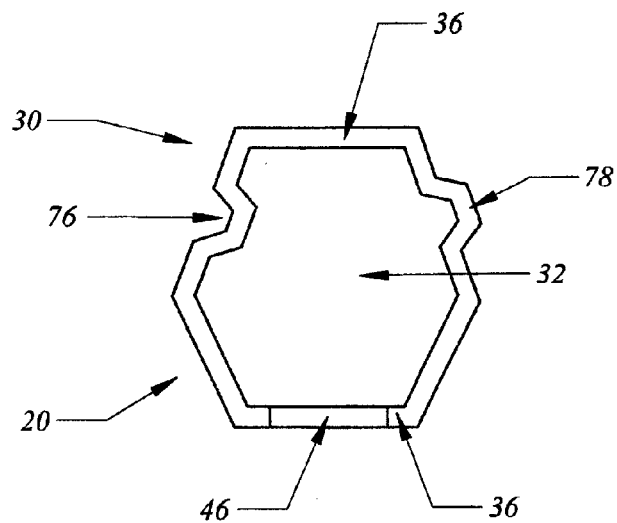
FIG. 5A enables a nebulous hexagonal polygonal body embodiment within the ambit of the present invention.

By way of illustration and not limitation, FIGS. 3A-5A are top plan views of preferred embodiments of stabilizers (20) with amorphous or nebulous shaped polygonal bodies (30). FIG. 3A portrays one of a plethora of nebulous rectangular-like polygonal bodies (30) having amorphous segment (72) associated with the wall of a rectangular-like polygonal body (30). FIG. 4A shows one of many potential nebulous trapezoidal-like polygonal bodies (30) including amorphous segment (74) associated with the wall of a trapezoidal-like polygonal body (30). FIG. 5A enables one or a plethora of hexagonal-like polygonal bodies (30) having amorphous segments (76 and 78) associated with the wall of a hexagonal-like polygonal body (30).

Figure 6:
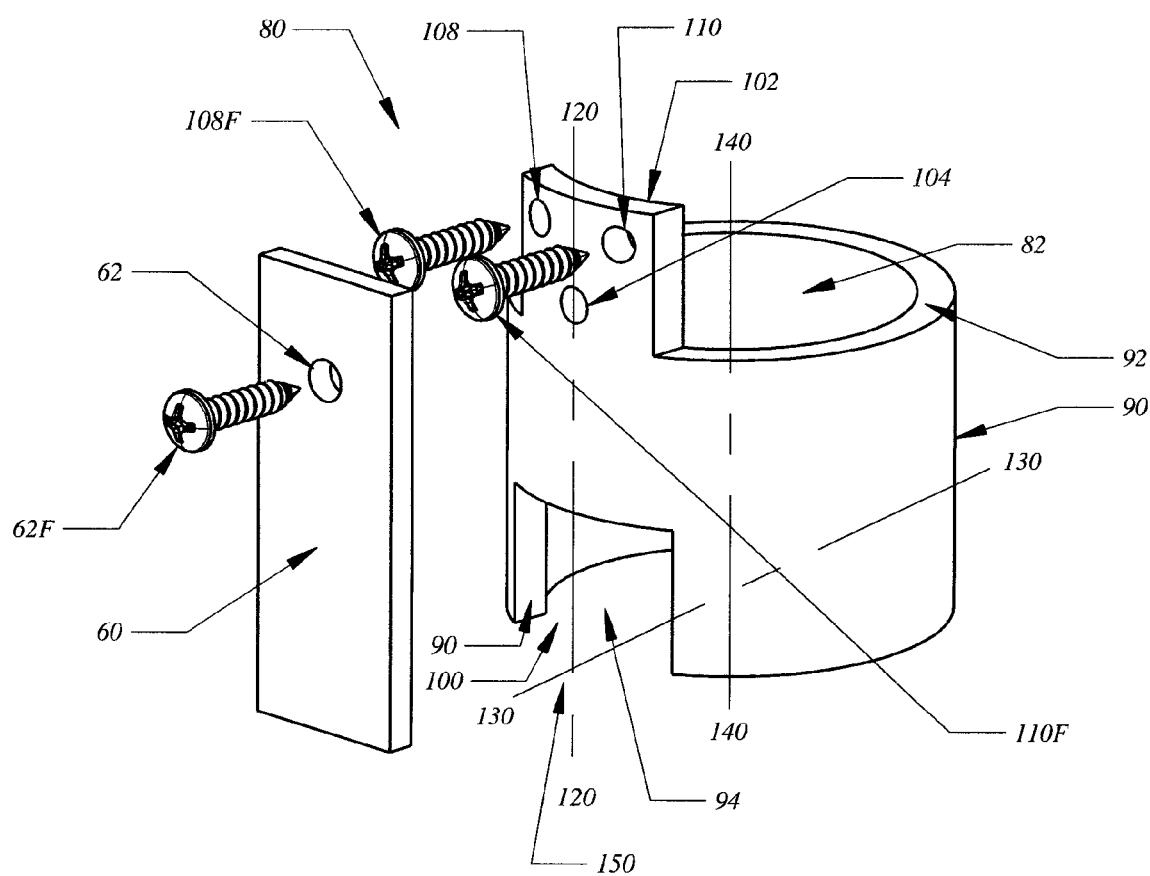
FIG. 6 portrays a preferred embodiment of a cylindrical or elliptic cylindrical stabilizer (80).

FIG. 6 portrays a preferred embodiment of a cylindrical or elliptic cylindrical stabilizer (80). Cylindrical or elliptic cylindrical wall (90) encloses lumen, cavity or tunnel (82). Rim (92) is distal from the load-bearing spinal implant. As shown FIGS. 6 and 17, gap (94) of cylindrical or elliptic cylindrical wall (90) is distal from rim (92) and proximate a longitudinal end of load bearing spinal implant (200). Gap (94) in cylindrical or elliptic cylindrical wall (90) creates socket (100) for fitting about a longitudinal end of the spinal implant.

Extension (102) extends beyond rim (92) in a lengthwise direction away from the load bearing spinal implant (200), where the direction is analogous or similar to the longitudinal axis of spinal implant (200). In select preferred embodiments, extension (102) is proximate to and coplanar with gap (94). Extension (102) is provided with apertures (104, 108 and 110). In select preferred embodiments, extension (102) follows the contour of rim (92). In still other select preferred embodiments, extension (102) is coplanar with central lengthwise axis (120-120) that intersects center (150) of gap

(94) and is simultaneously perpendicular to axis (130-130) that is simultaneously perpendicular to central lengthwise axis (140-140) wherein axis (130-130) intersects center (150) of gap (94). As shown in FIG. 6, cavity or tunnel (82) is open to rim (92), but in other select preferred embodiments a continuous surface covers cavity or tunnel (82) to create an end of stabilizer (80) that is enclosed rather than open.

Figure 17:
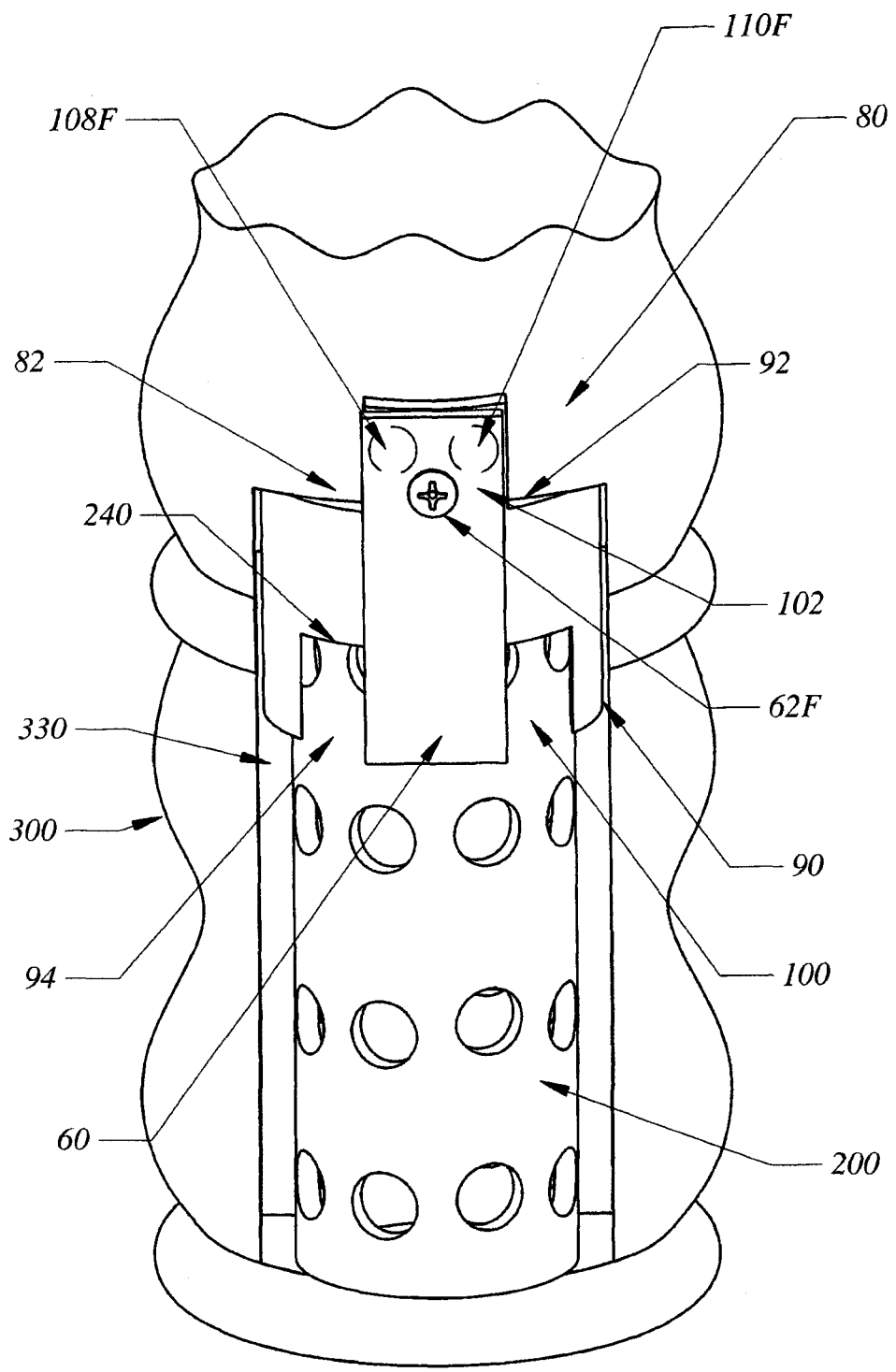
FIG. 17 is frontal view of a preferred embodiment of a cylindrical or elliptic cylindrical stabilizer (80) for assisting with stabilization of load-bearing spinal implant (200).

Cover (60) is provided with aperture (62) that upon attachment to extension (102) of wall (90) corresponds to aperture (104) of extension (102). When cover (60) is attached to stabilizer or body (80), cover (60) prevents egress of fasteners (108F and 110F) from extension (102) of wall (90). As shown in FIG. 17, fastener (62F) secures cover (60) at aperture (104) of extension (102) such that cover (60) blocks lateral egress of load-bearing spinal implant (200) from gap (94) and socket (100).

Figure 7:
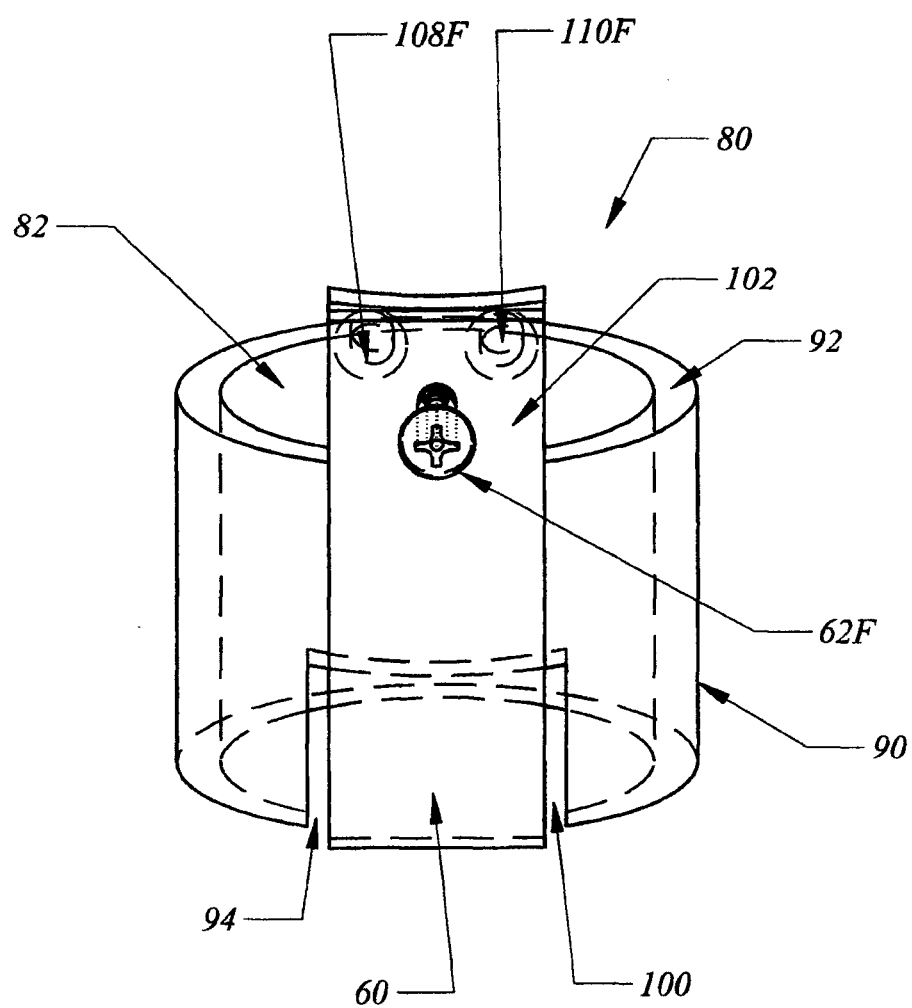
FIG. 7 is a frontal perspective of stabilizer (80) where cover (60) is attached to extension (102).

FIG. 7 is a frontal perspective of stabilizer (80) where cover (60) is attached to extension (102). Fastener (62) secures cover (60) to stabilizer or body (80) to block egress of fasteners (108F and 110F) from apertures (108 and 110), respectively. Cover (60) is of sufficient length to block egress of the spinal implant (not shown in this view) from gap (94) and socket (100).

Figure 8:
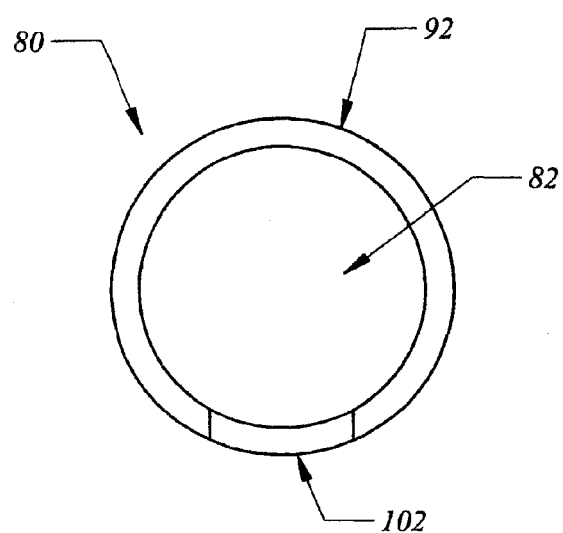
FIG. 8 is a top plan view of a preferred cylindrical body embodiment within the scope of the present invention.
Figure 9:
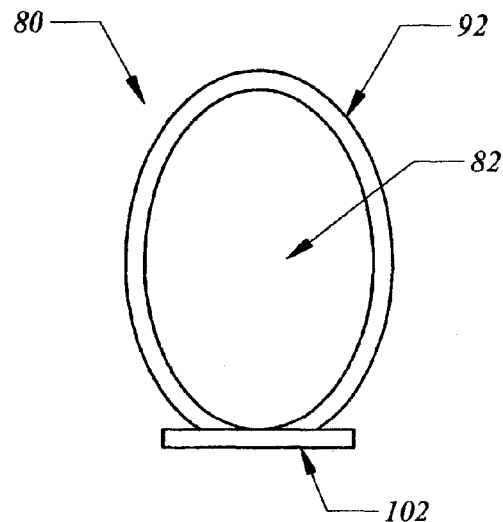
FIG. 9 is a top plan view of a preferred elliptic cylindrical body embodiment within the scope of the present invention.
Figure 10:
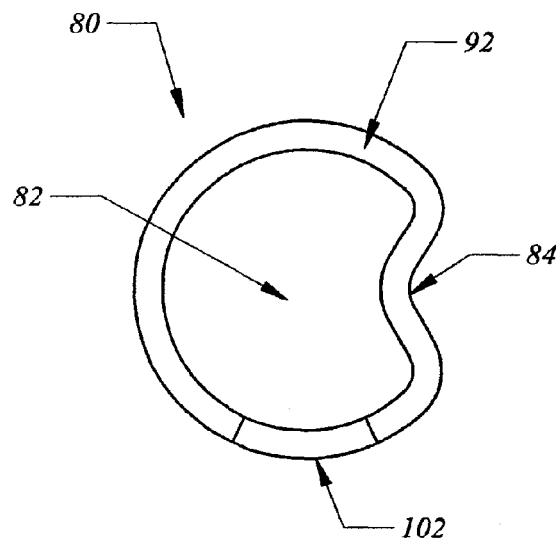
FIG. 10 is a top plan view of a nebulous cylindrical-like body embodiment within the scope of the present invention.
Figure 11:
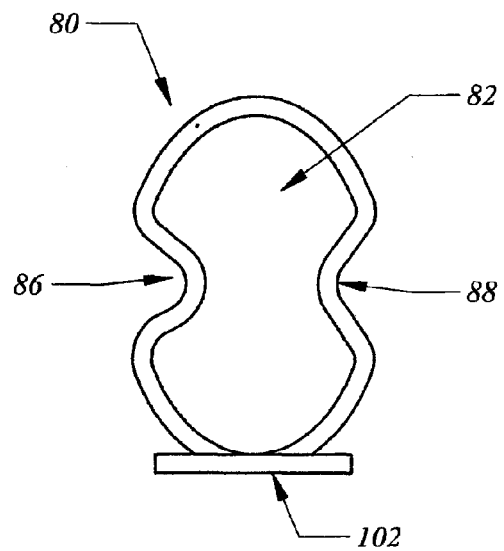
FIG. 11 is a top plan view of an elliptic cylindrical-like body embodiment within the scope of the present invention.

By way of illustration and not limitation, FIGS. 8-11 are top plan views of preferred embodiments of cylindrical or elliptic cylindrical stabilizer (80). FIG. 8 portrays cylindrical body (80) including lumen or tunnel (82), rim (92) and extension (102). FIG. 9 shows an elliptic cylindrical body (80) having lumen or tunnel (82), rim (92) and extension (102). FIG. 10 enables one of a plethora of nebulous cylindrical bodies (80) having lumen or tunnel (82), amorphous segment (84), rim (92) and extension (102). FIG. 11 shows one of a plethora of nebulous elliptic cylindrical bodies including lumen or tunnel (82), amorphous segments (86 and 88), rim (92) and extension (102).

Steps associated with the practice of the methods of embodiments the present invention are set forth in FIGS. 12-14. Those steps are related to the practice of using the stabilizer structures previously set forth.

FIG. 15 is a frontal view of a preferred embodiment of a polygonal stabilizer (20) for assisting with the stabilization of a spinal cage or other load-bearing spinal implant (200). Cover (60) is attached to anterior wall (42) of polygonal body (30) for assisting with stabilization of spinal implant (200). Depending upon surgical parameters, load-bearing spinal implant (200) can be of any structural dimension compatible with the size of cavity (330) that has been surgically created in a section of vertebra (300).

Perimeter (36) of polygonal body (30) is distal from longitudinal end (240) of load-bearing spinal implant (200). Extending from perimeter (36) toward spinal implant are lateral walls (40L and 40R) and posterior wall (38) (not shown in this view). Posterior wall (38) and lateral walls (40L and 40R) extend approximately identical lengths from perimeter (36). Anterior wall (42) has first section (44) extending from perimeter (36) toward load-bearing spinal implant (200) and second section or extension (46) extending from perimeter (36) away from a longitudinal end (240) of spinal implant (200). Since first section (44) is of lesser length than posterior wall (38) and lateral walls (40L and 40R), socket (50) for fitting about a longitudinal end (240) of spinal implant (200) is created. Longitudinal end (240) of load-bearing spinal implant (200) can be fitted through gap (48) into socket (50). Extension (46) of anterior wall (42) is provided with apertures (54, 56 and 58) (as shown in FIGS. 1 and 16.)

As shown in FIGS. 1, 2, 15 and 16, cover (60) is provided with aperture (62) that upon attachment to polygonal body (30) aligns with aperture (54) of second section (46) of anterior wall (42). When cover (60) is attached to polygonal body (30), cover (60) prevents egress of fasteners (56F and 58F) from second section (46) of polygonal body (30). Fasteners (56F and 58F) are also secured to vertebra (300), thereby securing stabilizer (20) to vertebra (300). Fastener (62F) secures cover (60) at aperture (54) to extension (46) such that longitudinal end (240) is circumscribed by socket (50) and cover (60). Stabilizer (20) blocks lateral egress of load-bearing spinal implant (200) from gap (48) and socket (50) of stabilizer (20) by surrounding longitudinal end (240) of spinal implant (200).

Figure 16:
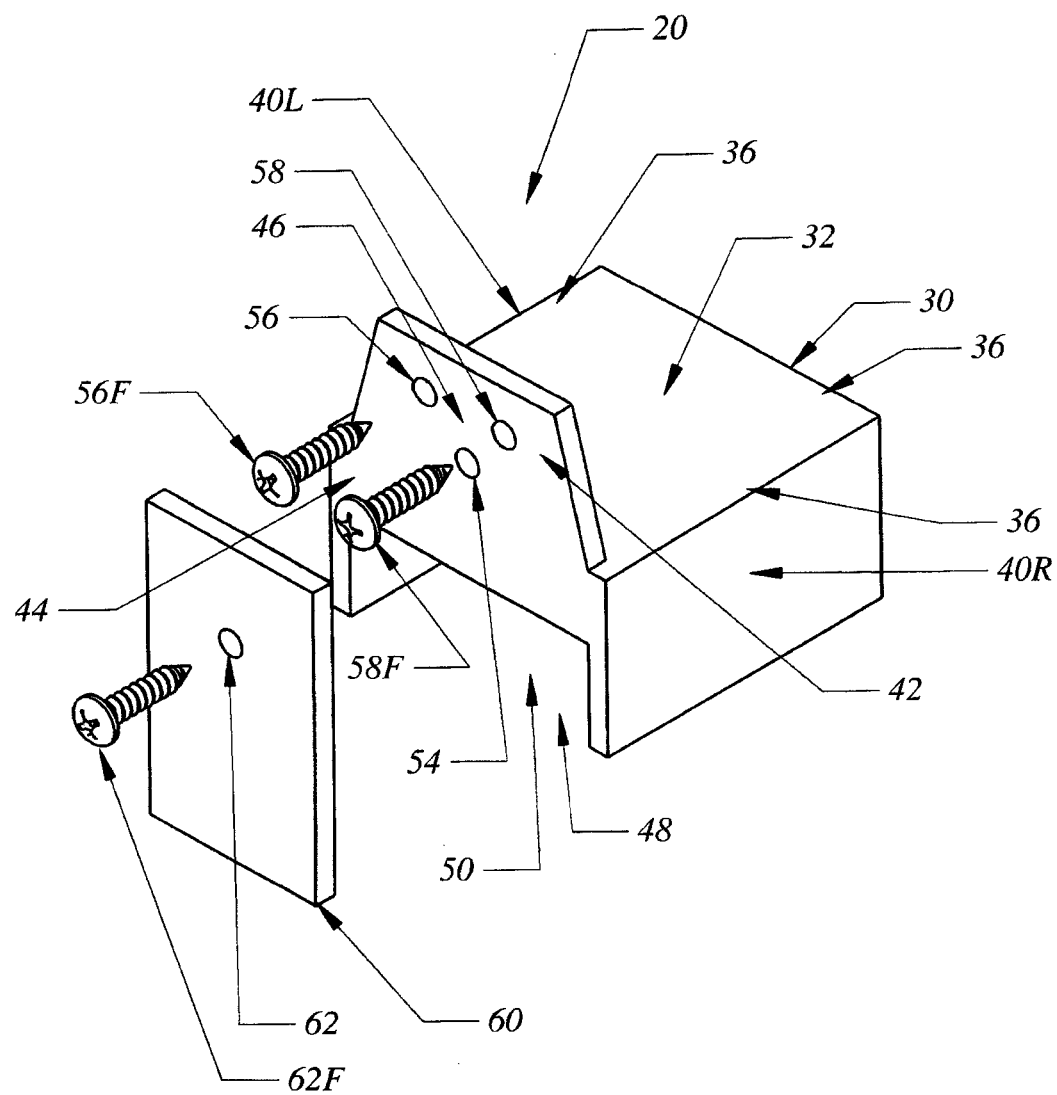
FIG. 16 is an exploded view frontal perspective of a preferred embodiment of the stabilizer (20) having a polygonal body (30) and attachable cover (60) similar to the stabilizer shown in FIG. 1.

FIG. 16 is an exploded view frontal perspective of a preferred embodiment of the stabilizer (20) having a polygonal body (30) and attachable cover (60) similar to the stabilizer shown in FIG. 1—the difference being that perimeter (36) is a continuous solid surface such that one end of opening (32) is closed.

FIG. 17 is a frontal view of a preferred embodiment of a generally cylindrical or generally elliptic cylindrical stabilizer (80) for assisting with stabilization of load-bearing spinal implant or cage (200). Cover (60) is attached to cylindrical or elliptic cylindrical body (80) to assist with the stabilization of load-bearing spinal implant (200). Depending upon surgical parameters, load-bearing spinal implant (200) can be of any design compatible with cavity (330) that has been surgically created in a section of vertebra (300).

Cylindrical or elliptic cylindrical wall (90) encloses lumen, cavity or tunnel (82). Rim (92) is distal from a longitudinal end (240) of load-bearing spinal implant (200). Gap (94) of cylindrical or elliptic cylindrical wall (90) is distal from rim (92) and proximate longitudinal end (240) of load-bearing spinal implant (200). Gap (94) in cylindrical or elliptic cylindrical wall (90) creates socket (100) for fitting about lengthwise end (240) of load-bearing spinal implant (200). Extension (102) extends beyond rim (92) in a direction away from longitudinal end (240) of load-bearing spinal implant (200), where the direction is analogous or similar to the longitudinal axis of the spinal implant. Extension (102) is provided with apertures (104, 108 and 110) (shown in FIG. 6). In select preferred embodiments, extension (102) follows the contour of rim (92), and in some preferred embodiments, extension (102) is integral with cylindrical or elliptic cylindrical wall (90) and coplanar with gap (94).

As shown in FIGS. 6, 7, 17 and 18, cover (60) is provided with aperture (62) that upon attachment to extension (102) of wall (90) corresponds to aperture (104) of extension (102). When cover (60) is attached to stabilizer (80), cover (60) prevents egress of fasteners (108F and 110F) from extension (102) of wall (90). Fasteners (108F and 110F) are also secured to vertebra (300). Fastener (62F) secures cover (60) at aperture (104) of extension (102) such that cover (60) blocks lateral egress of load-bearing spinal implant (200) from gap (94) and socket (100) of stabilizer (80). The combination of socket (100) and cover (60) circumscribe lengthwise end (240) of load-bearing spinal implant (200). Cover (60) is of sufficient length to block lateral egress of spinal implant (200) from gap (94) and socket (100) of stabilizer (80).

Figure 18:
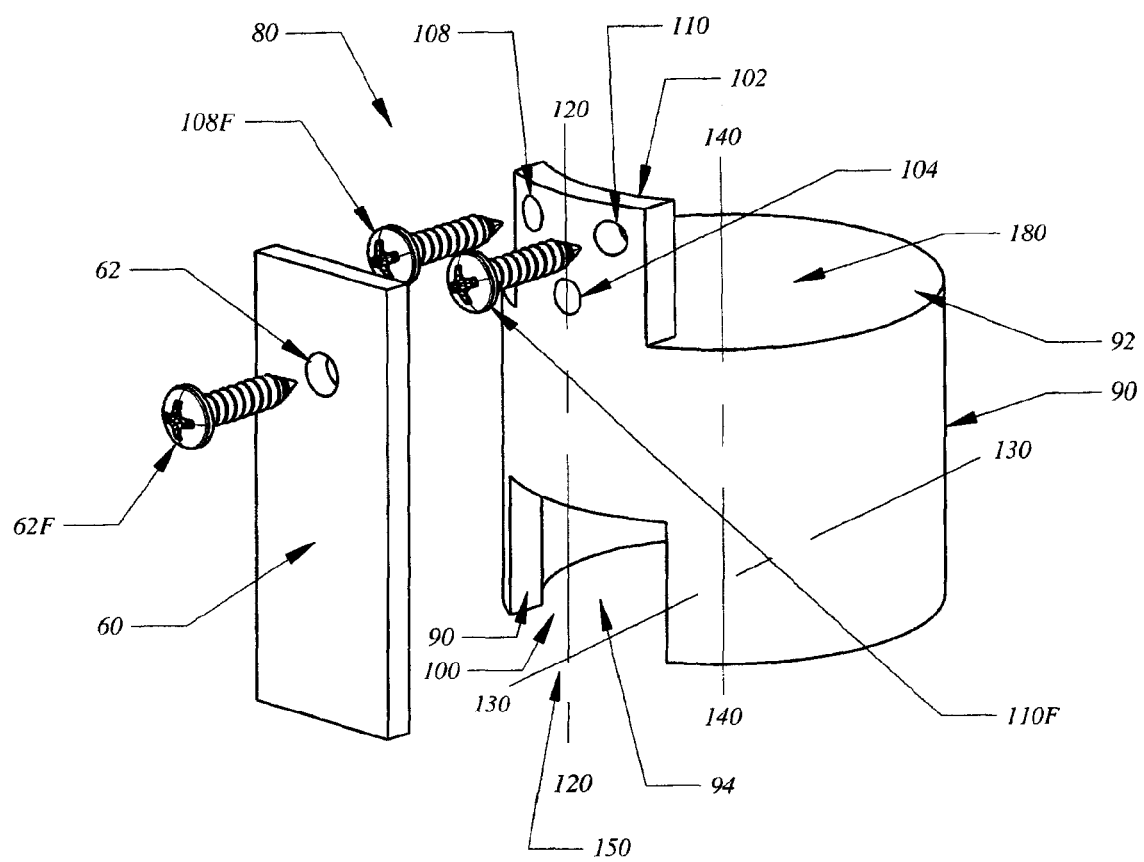
FIG. 18 is an exploded view frontal perspective of a preferred embodiment of the stabilizer (80) having a cylindrical or elliptic cylindrical wall (90) and attachable cover (60) similar to the stabilizer shown in FIG. 6.

FIG. 18 is an exploded view frontal perspective of a preferred embodiment of the stabilizer (80) having a cylindrical or elliptic cylindrical wall (90) and attachable cover (60) similar to the stabilizer shown in FIG. 6—the difference being that end (180) of stabilizer (80) is closed such that lumen or tunnel (82) is no longer open at one end of stabilizer (80).

Having disclosed the invention as required by Title 35 of the United States Code, Applicant now prays respectfully that Letters Patent be granted for his invention in accordance with the scope of the claims appended hereto.

What is claimed is:

1. A stabilizer assisting stabilization of a spinal cage implanted into a surgically created cavity; said stabilizer comprising:
   a) a body distinct from said spinal cage; said body comprising:
      i) a generally linear tunnel including a lengthwise axis, wherein said lengthwise axis runs in a similar direction with a longitudinal axis of said spinal cage;
      ii) a first end proximate a closest lengthwise edge of said spinal cage and a second end distal from said closet lengthwise edge;
      iii) a gap in said first end allowing lateral ingress and lateral egress of said closest lengthwise edge of said spinal cage such that a combination of said gap and said tunnel creates a socket securing a closest lengthwise edge of said spinal cage; and
      iv) an extension comprising a plurality of apertures and integral with said body, wherein said extension is opposed to and coplanar with said gap and extends beyond said second end in a direction analogous to said lengthwise axis;
   b) a cover comprising an aperture aligning with one of said extension's apertures and attachable to said extension, wherein said attached cover:
      i) blocks egress from a majority of said extension's apertures; and
      ii) blocks lateral egress of said spinal cage from said gap of said socket; and
   c) fasteners securing said cover to said extension and said extension to vertebra.

2. The stabilizer of claim 1, wherein said tunnel comprises a polygonal wall.

3. The stabilizer of claim 2, wherein said polygonal wall is rectangular.

4. The stabilizer of claim 3 further comprising an amorphous segment.

5. The stabilizer of claim 2, wherein said polygonal wall is trapezoidal.

6. The stabilizer of claim 5 further comprising an amorphous segment.

7. The stabilizer of claim 2, wherein said polygonal wall is hexagonal.

8. The stabilizer of claim 7 further comprising an amorphous segment.

9. The stabilizer of claim 2, wherein said tunnel further comprises a closed end proximate said extension.

10. The stabilizer of claim 1, wherein said tunnel comprises a cylindrical wall or an elliptic cylindrical wall.

11. The stabilizer of claim 10, wherein said cylindrical or an elliptic cylindrical wall further comprises an amorphous segment.

12. The stabilizer of claim 11, wherein said tunnel further comprises a closed end proximate said extension.

13. The stabilizer of claim 10, wherein said tunnel further comprises a closed end proximate said extension.

14. A stabilizer assisting stabilization of a load-bearing spinal implant implanted into a surgically created cavity; said stabilizer comprising a body distinct from said load-bearing spinal implant; said body further comprising:
   a) a wall surrounding a lumen, wherein said wall further comprises:
      i) first and second opposed lengthwise ends comprising openings corresponding to said lumen;
      ii) a rim distal from a closest longitudinal end of said load-bearing spinal implant;
      iii) a gap at said lengthwise ends proximate said load-bearing spinal implant allowing lateral ingress and egress of said closest longitudinal end of said load-bearing spinal implant, wherein a combination of said gap and said wall creates a socket securing said closest longitudinal end of said load-bearing spinal implant; and
      iv) an extension comprising a plurality of apertures, wherein said extension is opposed to said gap and extends beyond said rim distal from said closest longitudinal end of said load-bearing spinal implant in a direction similar to said lengthwise axis;
   b) a cover comprising an aperture aligning with one of said extension's apertures and attachable to said extension, wherein said attached cover:
      i) blocks egress from a majority of said extension's apertures; and
      ii) blocks lateral egress of said load-bearing spinal implant from said gap of said socket; and
   c) fasteners securing said cover to said extension and said extension to vertebra.

15. The stabilizer of claim 14, wherein said extension is coplanar with said gap.

16. The stabilizer of claim 15, wherein said wall is a cylindrical or an elliptic cylindrical wall.

17. The stabilizer of claim 16, wherein said cylindrical or said elliptic cylindrical wall further comprises a closed end.

18. The stabilizer of claim 16, wherein said cylindrical or an elliptic cylindrical wall further comprises an amorphous segment.

19. A stabilizer for assisting stabilization of a spinal cage implanted into a surgically created cavity, wherein said stabilizer is distinct from said spinal cage; said stabilizer comprising:
   a) a cylindrical or an elliptic cylindrical wall encircling a lumen, wherein said wall comprises a first lengthwise end, a second lengthwise end and a lengthwise axis; said wall further comprising:
      i) a rim at said first lengthwise end, wherein said rim is distal from a closest longitudinal end of said spinal cage;
      ii) an opening opposite said rim surrounding said closest longitudinal end of said spinal cage;
      iii) a gap at said second lengthwise end opposite said first lengthwise end allowing lateral ingress and lateral egress of said closest longitudinal end of said spinal cage, wherein a combination of said gap and said wall creates a socket securing said longitudinal end of said spinal cage; and
      iv) an extension comprising a plurality of apertures and integral with said wall, wherein said extension is opposed to and coplanar with said gap and extends beyond said rim in a direction analogous to said lengthwise axis;
   b) a cover comprising an aperture aligning with one of said extension's apertures and attachable to said extension, wherein said attached cover:
      i) blocks egress from a majority of said extension's apertures; and
      ii) blocks lateral egress of said spinal cage from said gap of said socket; and
   c) fasteners securing said cover to said extension and said extension to vertebra.

20. The stabilizer of claim 19, wherein said first lengthwise end is closed.

* * * * *